United States Patent [19]

D'Amico

[11] 4,097,260
[45] Jun. 27, 1978

[54] 2-SUBSTITUTED-1,3(2H,4H)-ISOQUINO-LINEDIONES AS PLANT GROWTH REGULANTS

[75] Inventor: John J. D'Amico, St. Louis, Mo.

[73] Assignee: Monsanto Company, St. Louis, Mo.

[21] Appl. No.: 636,012

[22] Filed: Nov. 28, 1975

[51] Int. Cl.$^2$ ............................................. A01N 9/22
[52] U.S. Cl. ............................................. 71/94; 71/74; 71/76; 71/77; 260/289 D
[58] Field of Search .................. 71/94, 76; 260/289 D

[56] References Cited

U.S. PATENT DOCUMENTS

| | | | |
|---|---|---|---|
| 3,247,212 | 4/1966 | Johnson | 71/94 |
| 3,732,232 | 5/1973 | Regel et al. | 71/94 |
| 4,013,445 | 3/1977 | Bellus et al. | 71/94 |

OTHER PUBLICATIONS

Otto, "Reactions of 1,4–pentadiene-3-ones" etc., (1974) CA80, No. 108328d, (1974).

Pfizer, "1,3 (2H,4H)-Dioxoisoquinoline" etc., (1968) CA70, No. 115025z, (1969).
Rosen et al., "Diazepines v. the Reaction", etc., (1969) J. Hetero Chem. 6, pp. 9–12 (1969).

*Primary Examiner*—Glennon H. Hollrah
*Attorney, Agent, or Firm*—Richard H. Shear; Donald W. Peterson

[57] ABSTRACT

Plant growth regulation of leguminous plants is achieved by applying to the plants a compound having the formula

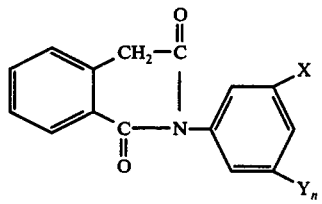

5 Claims, No Drawings

2-SUBSTITUTED-1,3(2H,4H)-ISOQUINOLINEDIONES AS PLANT GROWTH REGULANTS

The invention relates to a method of regulating the natural growth or development of plants by means of a chemical treatment. More specifically, the invention is directed to a method whereby the natural growth or development of leguminous plants, such as soybean, is regulated by applying to said plants an effective amount of an imide having the formula

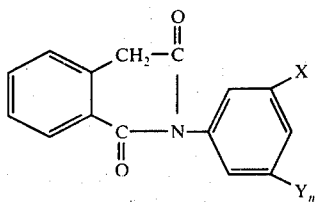

wherein X and Y are independently selected from the group consisting of trifluoromethyl, methoxy and chloro; and $n$ is zero or 1.

As used herein, the regulation of "plant growth or development" is understood to mean the modification of the normal sequential development of a treated plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color is illustrative of higher chloryphyll activity indicative of improved rate of photosynthesis.

Although phytotoxic amounts of the active ingredient may be employed to exert a herbicidal effect, the regulation of plant growth in accordance with the present invention does not include the total inhibition or killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium.

By the term "active ingredient" is meant the active imides of the foregoing formula. Preferred are those imides in which X and Y are identical substituents.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent or emulsifying agent or any suitable combination of these.

Illustrative finely divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well-known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, powder dusters, boom and hand sprayers and spray dusters. The composition can also be applied from airplanes as a dust or spray. Should the application of the plant growth composition to the plant growth medium be desired, this is accomplished by incorporating the compositions in the soil or other media in the area where modification of the plants is desired.

The quantity of active ingredient in the plant growth regulating composition varies upon the type of formulation, rate of application, plant to be treated, etc. Compositions of this invention generally contain from about 5 to 95 parts active ingredient, about 1 to 50 parts surface active agent and about 4 to 94 parts solvent, all parts being by weight based on the total weight of the composition. The specific quantity of active ingredient utilized, however, is well within the skill of the art.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts of from about 0.056 to about 11.2 or more kilos per hectare. Preferred are foliar applications of from 0.056 to 5.6 kilos of the active ingredient per hectare. In application to the soil habitat of germinant seeds, emerging seedlings and established vegetation for the regulation of plant growth, the active ingredients are applied in amounts of from 0.0112 to about 22.4 kilos per hectare or more. The application to the soil of from 0.112 to about 11.2 kilos of active ingredient per hectare is preferred. Foliar application to plants beginning to blossom are preferred over other types of applications.

In accordance with the practice of the invention, several plant growth regulating compositions were formulated utilizing various imides as the active ingredient. These compositions were formulated so that they could be applied in tests at a rate the equivalent of 302 liters per hectare. Table I illustrates the formulation of the composition for several application rates of active ingredient. In each formulation, the stock solution utilized is one percent of the active ingredient dissolved in acetone.

TABLE I

| RATE Lbs/Acre (kilos/hectare) | ml. of 1% Stock Solution | ml. Acetone | ml. 0.39% TWEEN 20 In Water As Surfactant |
|---|---|---|---|
| 6.0 (6.72) | 2.0 | — | 3.6 |
| 5.0 (5.60) | 2.0 | 1.0 | 3.7 |
| 3.0 (3.36) | 1.0 | 1.0 | 3.6 |
| 2.5 (2.80) | 1.0 | 2.0 | 3.7 |
| 1.2 (1.34) | 0.4 | 1.6 | 3.6 |
| 1.0 (1.12) | 0.4 | 2.6 | 3.7 |
| 0.6 (.672) | 0.2 | 1.8 | 3.6 |
| 0.5 (.560) | 0.2 | 2.8 | 3.7 |
| 0.3 (.336) | 0.1 | 1.9 | 3.6 |

Utilizing compositions formulated in accordance with TABLE I, several imides exhibited unexpected plant growth regulatory properties as illustrated by the test set forth in Example 1.

EXAMPLE 1

A number of soybean plants, variety Corsoy, are grown from seeds in aluminum pans in the greenhouse for a period of approximately 1 week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The composition as formulated in accordance with TABLE I is then applied to the pan of growing plants by overhead spray at a rate equivalent to the desired rate of active ingredient per acre. The treated pans, along with the control pans, are maintained in a greenhouse and watered from below on a sand bench and fertilized with a uniform portion of a water-soluble balanced fertilizer.

Two weeks after application of the chemical, the average height of the soybean plants in the treated pan is again measured as above and the difference in the average height before and 2 weeks after application represents the increase in the development of the treated pans. This development in growth to the treated plants is compared to the average increase in growth of the plants in the control pans during the same period of time. A variation of 25 percent or more in the development of at least two-thirds of the treated plants when compared to the development of the control plants demonstrates that the chemical is an effective plant regulant. Thus, a chemical is considered active when the treated plants manifest a decrease in growth of at least 25 percent less than that of the control plants, i.e., stature reduction, or an increase in growth in excess of twenty-five percent of that of the control plants, i.e., growth stimulation.

TABLE II below summarizes the results and observations made in accordance with Example 1 when the imides of the invention were utilized as the active ingredient at several rates.

TABLE II

| Compound | RATE Lbs/Acre (kilos/hectare) | Response |
|---|---|---|
| [structure: phthalimide with 3,4-dichlorophenyl group] | 6.0 (6.72) | Stature reduction, axillary bud development, rosette growth, chlorosis |
|  | 3.0 (3.36) | Stature reduction, axillary bud development, rosette growth, chlorosis |
|  | 1.2 (1.32) | Stature reduction, axillary bud development, rosette growth, chlorosis |
|  | 0.6 (.672) | Stature reduction, axillary bud development, rosette growth, chlorosis |
| [structure: phthalimide with 3-CF$_3$ phenyl group] | 6.0 (6.72) | Stature reduction, axillary bud development rosette growth |
|  | 30.0 (3.36) |  |
|  | 1.2 (1.32) |  |
|  | 0.6 (.672) |  |
| [structure: phthalimide with 3,5-bis(CF$_3$) phenyl group] | 6.0 (6.72) | Stature reduction, axillary bud development, altered canopy, slight leaf burn |
|  | 6.0 (6.72) | Stature reduction, axillary bud development, rosette growth, leaf inhibition |
|  | 3.0 (3.36) | Stature reduction, axillary bud development, rosette growth, leaf inhibition, chlorosis |
|  | 1.2 (1.32) | Stature reduction, axillary bud development, rosette growth, chlorosis |

TABLE II-continued

| Compound | RATE Lbs/Acre (kilos/hectare) | Response |
|---|---|---|
| *N-(2,5-dimethoxyphenyl) structure with CH₂-C(=O) and C(=O) linked to N-phenyl bearing OCH₃ groups (2,5-dimethoxyphenyl isoindoline-1,3-dione type)* | 6.0 (6.72) | Stature reduction, rosette growth, axillary bud development, slight leaf burn |
|  | 3.0 (3.36) | Stature reduction, axillary bud development, rosette growth |
|  | 1.2 (1.32) | Stature reduction, axillary bud development, rosette growth leaf alteration, slight leaf burn |
|  | 0.6 (.672) | Stature reduction auxillary bud development, leaf alteration rosette growth |
|  | 0.3 (.336) | Stature reduction, axillary bud development, leaf alteration, rosette growth |
| *N-(3,4,5-trimethoxyphenyl) isoindoline-1,3-dione analogue* | 0.12 (.132) | Stature reduction, axillary bud development leaf alteration, rosette growth, stem distortion |

Further advantages of this invention are shown in Example 2.

EXAMPLE 2

Individual soybean plants, variety Corsoy, are grown from seed in 6 inch pots containing a good grade of top soil. Two pots of 6-week old plants (5–6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and are fertilized with a uniform amount of a water-soluble balanced fertilizer. Two weeks after the application of the chemical, the growth responses of the treated plants are compared with that of the control plants. The total height of the plant is measured to the tip of the terminal bud. A variation of 15 percent in the average total height of the treated plants, when compared to the average total height of the control plants, demonstrates that the chemical is an effective plant growth regulator. Observations made utilizing the test procedure of Example 2 are summarized in TABLE III.

TABLE III

| Compound | RATE Lbs/Acre (kilos/hectare) | Response |
|---|---|---|
| *N-(2,5-dichlorophenyl) isoindoline-1,3-dione* | 1.00 (1.12) | Stature reduction, leaf distortion, stem distortion, altered canopy, axillary bud development, leaf alteration |
|  | 0.5 (.56) | Leaf distortion, stem distortion, leaf inhibition, inhibited pod set and development |
|  | 0.25 (.28) | Stature reduction |
| *N-(4-trifluoromethylphenyl) isoindoline-1,3-dione* | 1.0 (1.12) | Stature reduction, stem distortion, leaf distortion, altered canopy |
|  | 0.5 (.56) | Stature reduction, stem distortion, leaf distortion, altered canopy |
|  | 0.25 (.28) | Stature reduction, leaf distortion |
| *N-(4-trifluoromethylcyclohexyl) isoindoline-1,3-dione* | 2.5 (2.8) | Leaf distortion, stem distortion, altered canopy, inhibited pod set |
|  | 1.0 (1.12) | Stature reduction, stem distortion, leaf distortion, altered canopy |
|  | 0.5 (.56) | Stature reduction, leaf distortion |

TABLE III-continued

| Compound | RATE Lbs/Acre (kilos/hectare) | Response |
|---|---|---|
| 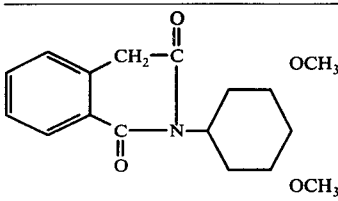 | 0.25 (.28)<br>0.10 (.112)<br>0.05 (.056) | Stature reduction, leaf distortion<br>Stature reduction<br>No response |

The imides of the invention may be prepared in accordance with reaction (A) below by heating a reaction mixture of homophthalic anhydride, the appropriate substituted aniline and acetic acid at reflux for the period of time specified in TABLE IV. TABLE IV summarizes the yields obtained when 16.2 g (0.1 moles) of homophthalic anhydride, 0.1 moles of the appropriate substituted aniline and 50 ml. of acetic acid were heated at reflux (115°–117° C.) for the time period specified. After allowing the stirred mixture to cool to room temperature, 500 to 600 ml. of water was added. Stirring at room temperature was continued for 30 minutes. The precipitate was collected by filtration, washed with water until the washings were neutral to litmus paper and air dried.

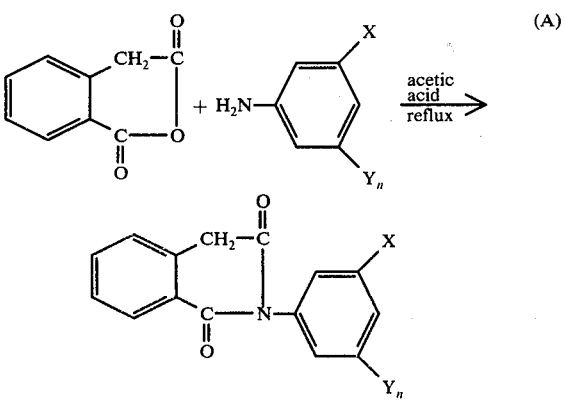

(A)

TABLE IV

| R | Hours Reflux Period | mp.° C. | % Yield | % C Calcd. | % C Found | % H Calcd. | % H Found | % N Calcd. | % N Found | % F Calcd. | % F Found | % Cl Calcd. | % Cl Found |
|---|---|---|---|---|---|---|---|---|---|---|---|---|---|
| 4-Cl-phenyl | 24 | 241[a] | 66 | 58.84 | 58.80 | 2.96 | 3.03 | 4.58 | 4.48 | | | 23.16 | 22.99 |
| 3-Cl-5-CF$_3$-phenyl | 1 | 141-2[b] | 85 | 62.95 | 62.84 | 3.30 | 3.17 | 4.59 | 4.52 | 18.67 | 18.75 | | |
| 3-CF$_3$-phenyl | 1 | 205-6[b] | 78 | | | | | 3.75 | 3.68 | 30.54 | 29.90 | | |
| 3-CF$_3$-5-OCH$_3$-phenyl (OCH$_3$) | 5 | 145-6[c] | 84 | 68.65 | 68.48 | 5.08 | 5.12 | 4.71 | 4.92 | | | | |

[a] Recrystallization from ethyl acetate.
[b] Recrystallization from isopropyl alcohol.
[c] Recrystallization from toluene.

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of regulating the growth of leguminous plants which comprises treating said plants with an effective non-lethal amount of a compound having the formula

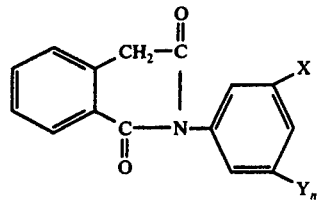

wherein X and Y are selected from the group consisting of trifluoromethyl, methoxy and chloro; and $n$ is 0 or 1.

2. A method according to claim 1 wherein X and Y are the identical substituent.

3. A method according to claim 1 wherein said plants are soybeans.

4. A method according to claim 1 wherein X and Y are methoxy.

5. A method according to claim 1 wherein X and Y are chloro.